United States Patent [19]

Raja et al.

[11] Patent Number: 5,767,320
[45] Date of Patent: Jun. 16, 1998

[54] PROCESS FOR THE OXIDATION OF CYCLOHEXANE TO A MIXTURE OF CYCLOHEXANONE AND CYCLOHEXANOL

[75] Inventors: Robert Raja; Paul Ratnasamy, both of Maharashtra, India

[73] Assignee: Council of Scientific & Industrial Research, New Delhi, India

[21] Appl. No.: 687,839

[22] Filed: Jul. 26, 1996

[30] Foreign Application Priority Data

Sep. 29, 1995 [IN] India ............... 1791/DEL/95

[51] Int. Cl.$^6$ ............... C07C 45/33
[52] U.S. Cl. ............... 568/360; 568/342; 568/836
[58] Field of Search ............... 568/342, 360, 568/836

[56] References Cited

U.S. PATENT DOCUMENTS

| | | | |
|---|---|---|---|
| 3,974,221 | 8/1976 | Duggan | 568/360 |
| 4,568,769 | 2/1986 | Yoshima et al. | 568/360 |
| 4,659,829 | 4/1987 | Saussine et al. | 568/342 |
| 5,004,837 | 4/1991 | Baur et al. | 568/342 |
| 5,149,880 | 9/1992 | Sawyer et al. | 568/360 |
| 5,233,092 | 8/1993 | Zaosheng | 568/360 |

*Primary Examiner*—James H. Reamer
*Attorney, Agent, or Firm*—Ladas & Parry

[57] ABSTRACT

Cyclohexane is oxidized to a mixture of cyclohexanone and cyclohexanol by reaction with oxygen in the presence of a metal complex of phthalocyanine or porphyrin wherein some or all of the hydrogen atoms of the phthalocyanine or porphyrin have been replace by electron withdrawing groups.

11 Claims, No Drawings

PROCESS FOR THE OXIDATION OF CYCLOHEXANE TO A MIXTURE OF CYCLOHEXANONE AND CYCLOHEXANOL

FIELD OF INVENTION

This invention relates to an improved process for the oxidation of cyclohexane to a mixture of cyclohexanone and cyclohexanol. More particularly the present invention relates to an improved process for the oxidation of cyclohexane to a mixture of cyclohexanone and cyclohexanol, using molecular oxygen as the oxidant and a solid organotransition metal complex as a catalyst.

BACKGROUND OF INVENTION

Cyclohexanol and cyclohexanone are major commodity chemicals used as an intermediates in the manufacture of adipic acid, nylon 6,6, urethane foams, acidulant in baking powder and lubricating additives. The great majority of cyclohexanone and cyclohexanol on the market is made from cyclohexane, generally via KA oil which is a mixture of cyclohexanol and cyclohexanone. Adipic acid is made by a two step process from cyclohexane, via cyclohexanol and cyclohexanone. In the first step cyclohexane is oxidized at a temperature range 150° to 175° C. and a pressure of 115 to 175 psi in the presence of a soluble catalyst like cobalt napthenate or octoate in a concentration of 0.3 to 3 ppm, to a mixture of cyclohexanol and cyclohexanone. Conversions are usually in the range of 3 to 8% with selectivities in the range of 70 to 80%. In the second step, the mixture of cyclohexanol and cyclohexanone, which are formed by the oxidation of cyclohexane in the first step, are oxidized by nitric acid to adipic acid. Numerous byproducts are also formed during these reactions. The byproducts include formic acid, butyric acid, valeric acid, caproic acid, etc. In addition gaseous byproducts like carbon monoxide and dioxide are also formed, like carbon monoxide and dioxide are also formed.

There have been many references in the prior art, to the one step molecular oxygen oxidation of cyclohexane to cyclohexanone and cyclohexanol. Japanese Patent No. 45-16444 claims the oxidation of cyclohexane in acetic acid using cobalt acetate and acetaldehyde as catalysts at 80° C., oxygen at 225 psi, giving a conversion of 96% and a selectivity to cyclohexanone and cyclohexanol of 70%. British Patent 1,143,213 claims the oxidation of cyclohexane at 114° to 119° C., 250 psi in acetic and propionic acid using manganese stearate as catalyst. U.S. Pat. No. 4,263,453 claims oxidation of cyclohexane at 95° C., 300 psi in acetic acid containing a little water and using cobalt acetate as a catalyst giving a conversion of 92% and a selectivity to cyclohexanone and cyclohexanol of 80%.

There are many drawbacks in the single step process for the oxidation of cyclohexane to a mixture of cyclohexanone and cyclohexanol mentioned hereinabove and because of this in commercial practice worldwide heterogenous catalysts are used extensively. One drawback in such processes is the low level (3–5%) of cyclohexane conversion necessitating the large recycle (more than 95%) of unreacted cyclohexane incurring thereby an expenditure of a large amount of process energy. A second major disadvantage of such processes is the use of nitric acid in the process. Large amounts (mole equivalent of nitric acid used) of nitrogen oxide vapors are released in the process which constitute an environmental hazard. Yet another drawback of the single step prior art processes is the large amount of liquid and gaseous byproducts formed leading to severe problems in their disposal. Eventhough many of these processes are practiced commercially, all of them suffer from high cost due to both such multi step operations and the use of nitric acid as well as from pollution problems caused by the discharge of ozone depleting nitrogen oxide byproducts mentioned hereinabove.

Other process options for the manufacture of mixture of cyclohexanone and cyclohexanol without the use of nitric acid have been proposed, as for example in U.S. Pat. No. 3,390174 and British patent No. 1,304,855. However, the air oxidation processes proposed in these patents are multi step processes with poor selectivity (in the range 30–50%) and require difficult high cost recovery process for cyclohexanone and cyclohexanol. An additional problem in all the prior art processes using molecular oxygen or air as oxidant and soluble homogeneous catalysts is the necessity to recover or dispose off the soluble metal catalysts that are used in such processes. Hence an air oxidation process that provides good yields of cyclohexanol and cyclohexanone free of significant byproducts, such as succinic, glutaric and caproic acids and using a solid oxidation catalyst will be highly desirable. Until now however the seemingly attractive direct oxidation routes using molecular oxygen have not proven to be commercially and environmentally viable probably because of the soluble metal catalysts, such as cobalt acetate and cobalt napthenate used therein, as well as the low conversion (3–5%) and selectivity (30–50%) obtained in such processes. A review of the known single stage oxidation processes using homogeneous catalysts for the preparation of mixture of cyclohexanone and cyclohexanol from cyclohexane are discussed by K. Tanaka et al in the journals Chemtech, 555–559 (1974) and Hydrocarbon Processing, 53,114–120 (1974). Additional references for the single step direct oxidation of cyclohexane to mixture of cyclohexanone and cyclohexanol using soluble homogeneous catalysts include U.S. Pat. Nos. 3,231,608; 2,589,648; 4,032,569; 4,263,453; 4,158,739; 5,321,157; as well as the article by G. N. Kulsrestha et al in Chem. Tech. Biotechnol., 50, 57–65 (1991).

The use of solid catalyst in the oxidation of cyclohexane to a mixture of cyclohexanone and cyclohexanol is known in the prior art. F. T. Starzyk et al reported in the journal Studies in Surface Science and Catalysis Vol. 84, pages 1419–1424 (1994) that using tertiary butyl hydroperoxide, but not molecular oxygen, as the source of oxygen and iron phthalocyanine encapsulated in Y zeolite as the catalyst, cyclohexane could be oxidized to cyclohexanone and cyclohexanol. One significant drawback of the process was the very slow rates of oxidation of cyclohexane thereby rendering the process commercially not attractive. FIG. 2 of the article of Starzyk et al mentioned hereinabove, for example, teaches that 300 hours of reaction time are needed to achieve a cyclohexane conversion of about 35% at 60° C. Moreover, significant quantities of cyclohexanone and cyclohexanol started appearing in the liquid product only after about 600 hours, the major products being hydroxy ketone upto this time. Kraushaar et al in European Patent 519,569 (1992) and Lin, S. S. and Weng, H. S. in the Journal of Applied Catalysis, Vol. A (105) page 229 (1993) have claimed the use of a cobalt-substituted aluminophosphate-5 as a heterogeneous catalyst for the auto-oxidation of cyclohexane in acetic acid as solvent. The intermediate cyclohexanol is converted to the more stable cyclohexylacetate. Hence, this system suffers from the inherent disadvantages of requiring acetic acid solvent and separate hydrolysis and dehydrogenation steps. R. A. Sheldon et al have recently claimed in International Patent PCT/NL 94/6319 (1994) and in the article in Journal of Catalysis, Vol. 153, pages 1-8 (1995) that chromium substituted aluminophosphate-5 is a heterogeneous catalyst for the oxidation of cyclohexane at 115°-130° C., 75 psi O₂ and 300 psi air in the presence of a small amount of an alkylhydroperoxide initiator to yield cyclohexanone as the major product. Cyclohexane conversion levels were in the range, 3-10% wt, cyclohexanone and cyclohexanol, the former in predominant proportions, were the main products. Significant quantities of byproducts, mainly dibasic acids like succinic, glutaric and adipic acids were also produced due to the high temperatures of the reaction.

It is thus evident from the above that there is a need for the development of a process for the oxidation of cyclohexane to a mixture of cyclohexanone and cyclohexanol in significant yields (at least 10-15% wt, for example) using solid, recyclable catalysts and operating at a low enough temperature (below 100° C., for example) to avoid the production of undesirable byproducts like succinic, glutaric, caproic and hydroxy caproic acids.

SUMMARY OF INVENTION

It is, therefore, an object of the present invention to provide an improved process for the preparation of a mixture of cyclohexanone and cyclohexanol by the oxidation of cyclohexane using a catalyst which would remain in the solid state at the end of the oxidation reaction thereby facilitating the easy separation, recovery and recycle of the catalyst from the reaction products without having any adverse impact on the environment.

Another object of the present invention is to provide an improved process whereby the yield of the mixture of cyclohexanone and cyclohexanol would be higher than in the prior art processes.

Yet another objective of the present invention is to provide an improved process for the preparation of a mixture of cyclohexanone and cyclohexanol at a temperature below that wherein a large number of byproducts due to thermal oxidation of cyclohexane, cyclohexanol and cyclohexanone reactions are generated.

Pthalocyanines consist of large, planar, conjugated, ring systems which serve as tetradentate ligands. Metallic cations can be easily accommodated at the center of these systems with the four nitrogens as the ligating atoms. Metal containing pthalocyanine compounds are known to be useful as chemical reagents of a catalytic nature, more particularly in directing certain oxidative processes. Many known pthalocyanines have been judged to suffer certain drawbacks by being deficient in the combination of properties desired for many candidate uses, such as in the oxidation of alkanes and more particularly in the oxidation of cyclohexane. One major drawback of homogeneous pthalocyanine catalysts in industrial oxidation processes is the formation of aggregates in solution which significantly deactivates these catalysts.

Due to our continued research in this area we observed that the organotransition metal complexes used as catalysts are solids insoluble in cyclohexane or the reaction products arising from oxidation of cyclohexane. Hence they do not undergo aggregation or change of phase during the oxidation wherein such changes are known to lead to catalyst deactivation problems.

Another drawback of pthalocyanines used in the prior art as catalysts for alkane oxidation is their low oxidative stability which is due to the easy oxidizability of the hydrogen atoms attached to the nucleus of the pthalocyanines.

We have found that the oxidative stability as well as the catalytic activity of the metal pthalocyanines used as catalysts in the oxidation of cyclohexane are enhanced by replacing the hydrogens from the pthalocyanines by electron withdrawing groups like the halogens, nitro or cyano groups thereby rendering the metal ions easier to reduce leading to an improved oxidation activity and stability of the catalysts during the reaction.

There are a total of 16 hydrogen atom positions on such pthalocyanine molecules which can in principle, be substituted by other substituents. We have observed that when some or all of the hydrogen atoms of the said pthalocyanines are substituted by one or more electron withdrawing groups such as halogen, nitro or cyano groups or mixtures of such groups there is substantial improvement in selectivity and conversion to a mixture of cyclohexanone and cyclohexanol.

Accordingly, the present invention provides an improved process for the oxidation of cyclohexane to a mixture of cyclohexanone and cyclohexanol which comprises reacting cyclohexane with molecular oxygen in the presence of a solid catalyst consisting of an organotransition metal complex wherein some or all of the hydrogen atoms of the said organotransition metal complex have been substituted by one or more electron withdrawing groups, at a temperature in the range of 20° C. to 80° C., at a pressure in the range of 5 to 1000 psi pressure, in the presence or absence of solvents, with or without a promoter and isolating the cyclohexanone and cyclohexanol formed by conventional methods.

In an embodiment of the present invention the organotransition metal complex is selected from pthalocyanines and porphyrins.

In another embodiment of the present invention, the transition metal is selected from iron, cobalt, copper, chromium, manganese or mixtures thereof.

Some nonlimiting examples of such organo transition metal complexes used as catalysts in the oxidation of cyclohexane to a mixture of cyclohexanone and cyclohexanol are iron halopthalocyanines, copper, halo pthalocyanines, cobalt halo pthalocyanines, chromium halo pthalocyanines, manganese halo pthalocyanines, iron nitro pthalocyanines, copper nitro pthalocyanines, chromium nitro pthalocyanines, cobalt nitro pthalocyanines, manganese nitro pthalocyanines, manganese cyano pthalocyanines, copper cyano pthalocyanines and chromium cyano pthalocyanines.

In yet another embodiment of present invention the electron withdrawing groups attached to the organotransition metal complex is selected from the halogens, fluorine, chlorine, bromine or iodine or the nitro or cyano groups.

In a preferred embodiment of the present invention, the oxidation of cyclohexane by molecular oxygen is catalyzed by the halogen, cyano or nitro pthalocyanines of the metals iron, cobalt, copper, chromium or manganese.

In yet another embodiment of the present invention, the source of molecular oxygen can be pure oxygen gas, air or a mixture of oxygen and an inert gas like nitrogen.

In yet another embodiment of the present invention, the above mentioned oxidation reaction can be carried out in the presence or absence of solvents. It may be an advantageous option to carry out the said oxidation reaction in the presence of a suitable solvent which would maintain the oxidation products like cyclohexanone and cyclohexaniol in the dissolved state during the course of the reaction, thereby facilitating the separation of the said mixtures of cyclohexanone and cyclohexanol from the solid catalysts. Suitable solvents for such use include acetonitrile, methanol, water, butanol and cyclohexanol. Examples of such solvents which can be used in the process of the present invention include acetonitrile, acetone, benzene or any other organic solvent which is inert under the oxidation reaction conditions.

In one advantageous embodiment of the present invention, the rates of the oxidation of cyclohexane to a mixture of cyclohexanone and cyclohexanol may be significantly enhanced by addition of very small catalytic quantities of a promoter. Examples of such promoters include alkyl hydroperoxide, dialkylperoxides and such compounds. Cyclohexylhydroperoxide, cumyl peroxide, tertiary butyl hydroperoxide are some of the examples of such promoters which may be present in concentrations not exceeding 1% by weight of cyclohexane and more preferably 0.1% by weight of cyclohexane.

In yet another advantageous embodiment of the present invention, the organotransition metal complex may be encapsulated in a solid matrix. Due to the greater dispersion of the organotransition metal complex catalyst in solid matrices and the consequent enhanced stability of the structural integrity of the catalyst significant process advantages like greater activity, stability and easy recovery and recyclability of the catalyst are observed. Examples of such solid matrices include inorganic oxide like silica, alumina, molecular sieves, zeolites and the like as well as organic polymeric material.

It is an advantageous feature of the process of the present invention that due to the high activity the catalysts used herein, the oxidation reaction can be carried out at temeratures much below those used in the prior art and preferably below 80° C., thereby leading to much lower yields of undesired side products like succinic, glutaric and caproic acids.

DETAILED DESCRIPTION

The details of the present invention is described in the examples given below which are provided by way of illustration only and therefore should not be construed to limit the scope of the invention.

EXAMPLE 1

In an autoclave, 7.5 g of cyclohexane and 0.75 g of solid iron tetra deca bromo pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy. The conversion of cyclohexane was 9% wt and the yield of the mixture of cyclohexanone and cyclohexanol was 7% wt.

EXAMPLE 2

In an autoclave, 7.5 g of cyclohexane and 0.75 g of solid cobalt tetra deca chloro pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy. The results are given in Table 1.

EXAMPLE 3

In an autoclave, 7.5 g of cyclohexane and 0.75 g of solid copper tetra deca chloro pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy. The results are given in Table 1.

EXAMPLE 4

In an autoclave, 7.5 g of cyclohexane and 0.75 g of solid chromium tetra deca fluoro pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy. The results are given in Table 1.

EXAMPLE 5

In an autoclave, 7.5 g of cyclohexane and 0.75 g of solid manganese tetra deca fluoro pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy. The results are given in Table 1.

Table 1 indicates the wt % conversion of cyclohexane and the wt % yield of cyclohexanol plus cyclohexanone when using different organotransition metal complexes as catalysts and using the conditions mentioned herein above (Examples 2–5).

TABLE 1

| Pthalocyanine | Ex-2 Cobalt | Ex-3 Copper | Ex-4 Chromium | Ex-5 Manganese |
|---|---|---|---|---|
| Conv. cyclohexane % wt | 9 | 11 | 8 | 10 |
| Yield of % wt cyclohexanone plus cyclohexanol | 7 | 9 | 6 | 9 |

EXAMPLE 6

In an autoclave, 7.5 g of cyclohexane and 0.75 g of solid iron deca nitro pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy. The results are given in Table 2.

EXAMPLE 7

In an autoclave, 7.5 g of cyclohexane and 0.75 g of solid cobalt deca nitro pthalocyanine were stirred at 50° C. with a continuous bubbling of air for 8 hrs. At the end of the reaction, 10 ml of methanol was added to the products (unreacted cyclohexane, cyclohexanol, cyclohexanone and cyclohexanone and cyclohexanol) which were then separated from the solid catalyst by centrifugation and analyzed by gas chromatography using a carbowax column and flame ionization detector (FID). The identity of the products was confirmed by GC mass spectroscopy. The results are given in Table 2.

EXAMPLE 8

In an autoclave, 7.5 g of cyclohexane and 0.75 g of solid copper deca nitro pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy.

The results are given in Table 2.

EXAMPLE 9

In an autoclave, 7.5 g of cyclohexane and 0.75 g of solid chromium deca nitro pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy.

The results are given in Table 2.

EXAMPLE 10

In an autoclave, 7.5 g of cyclohexane and 0.75 g of solid manganese deca nitro pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy. The results are given in Table 2.

Table 2 indicates the wt % conversion of cyclohexane, and the wt % yield of cyclohexanol plus cyclohexanone when using different organotransition metal complexes as catalysts and using the conditions mentioned herein above (Examples 6–10).

TABLE 2

| Pthalocyanine | Ex-6 Fe | Ex-7 Co | Ex-8 Cu | Ex-9 Cr | Ex-10 Mn |
|---|---|---|---|---|---|
| Cyclohexane conv, % wt | 15 | 13 | 18 | 12 | 16 |
| Yield of % wt cyclohexanone plus cyclohexanol | 11 | 10 | 17 | 10 | 14 |

EXAMPLE 11

In an autoclave, 7.5 g of cyclohexane and 0.75 g of solid iron tricyano pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy using standard compounds. The yield of the mixture of cyclohexanone plus cyclohexanol was 13% wt.

EXAMPLE 12

In an autoclave, 7.5 g of cyclohexane and 0.75 g of solid cobalt tricyano pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy using standard compounds. The yield of the mixture of cyclohexanone and cyclohexanol was 16% wt.

EXAMPLE 13

In an autoclave, 7.5 g of cyclohexane and 0.75 g of solid copper tricyano pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy. The yield of the mixture of cyclohexanone and cyclohexanol was 18% wt.

EXAMPLE 14

In an autoclave, 7.5 g of cyclohexane and 0.75 g of solid chromium cyano pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy. The yield of the mixture of cyclohexanone and cyclohexanol was 21% wt.

EXAMPLE 15

In an autoclave, 7.5 g of cyclohexane and 0.75 g of solid manganese cyano pthalocyanine were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy. The yield of the mixture of cyclohexanone and cyclohexanol was 19% wt.

EXAMPLE 16

In an autoclave, 7.5 g of cyclohexane, 0.75 g of solid iron tetra deca bromo pthalocyanine, 5 g of acetonitrile solvent, and 0.08 g of tert. butyl hydroperoxide promoter were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy using standard compounds. The conversion of cyclohexane was 28% and the yield of the mixture of cyclohexanone and cyclohexanol was 26% wt.

EXAMPLE 17

In an autoclave, 7.5 g of cyclohexane, 0.75 g of solid iron tetra deca chloro pthalocyanine, 5 g of methanol solvent, and 0.08 g of tert. butyl hydroperoxide promoter were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy. The conversion of cyclohexane was 32% and the yield of the mixture of cyclohexanone and cyclohexanol was 28% wt.

EXAMPLE 18

In an autoclave, 7.5 g of cyclohexane, 0.75 g of solid copper tetra deca chloro pthalocyanine, 5 g of methanol solvent, and 0.08 g of ditert. butyl peroxide promoter were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy The conversion of cyclohexane was 34% and the yield of the mixture of cyclohexanone and cyclohexanol was 32% wt.

EXAMPLE 19

In an autoclave, 7.5 g of cyclohexane, 1.25 g of solid copper tetra deca bromo pthalocyanine encapsulated in the aluminosilicate molecular sieve-Y, 5 g of methanol solvent, and 0.08 g of ditert. butyl peroxide promoter were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy. The conversion of cyclohexane was 32% and the yield of the mixture of cyclohexanone and cyclohexanol was 29% wt.

EXAMPLE 20

In an autoclave, 7.5 g of cyclohexane, 1.25 g of solid copper tetra deca chloro pthalocyanine encapsulated in an organic polymer, 5 g of methanol solvent, and 0.08 g of ditert. butyl peroxide promoter were stirred at 50° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy using standard compounds. The conversion of cyclohexane was 28% and the yield of the mixture of cyclohexanone and cyclohexanol was 24% wt.

EXAMPLE 21

In an autoclave, 7.5 g of cyclohexane and 0.75 g of solid iron tetra chloro porphyrin were stirred at 60° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography using a carbowax column and flame ionization detector (FID). The identity of the products was confirmed by GC mass spectroscopy using standard compounds. The conversion of cyclohexane was 16% and the yield of the mixture of cyclohexanone and cyclohexanol was 12.5% by wt.

EXAMPLE 22

In an autoclave, 7.5 g of cyclohexane, 1.25 g of solid manganese hexachloro tetraphenyl porphyrin, 0.1 g of tertiary butyl hydroperoxide and 5 g of acetonitrile were stirred at 60° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatography Using a carbowax column and flame ionization detector (FID). The identity of the products was confirmed by GC mass spectroscopy. The conversion of cyclohexane was 16% and the yield of the mixture of cyclohexanone and cyclohexanol was 15% by wt.

EXAMPLE 23

In an autoclave, 7.5 g of cyclohexane, 1.25 g of solid manganese hexachloro porphyrin encapsulated in the aluminosilicate molecular sieve-Y, 5 g of methanol solvent, and 0.08 g of ditert. butyl peroxide promoter were stirred at 60° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatogeraphy using a carbowax column and flame ionization detector (FID). The identity of the products was confirmed by GC mass spectroscopy. The conversion of cyclohexane was 36% and the yield of the mixture of cyclohexanone and cyclohexanol was 30% wt.

EXAMPLE 24

In an autoclave, 7.5 g of cyclohexane, 1.25 9 of solid manganese hexachloro porphyrin encapsulated in an organic polymer, 5 g of methanol solvent, and 0.1 g of ditert. butyl peroxide promoter were stirred at 60° C. with a continuous bubbling of air for 8 hrs. At the end of the reaction, 10 ml of methanol was added to the products (unreacted cyclohexane, cyclohexanone and cyclohexanol) which were then separated from the solid catalyst by centrifugation and analyzed by gas chromatogeraphy using a carbowax column and flame ionization detector (FID). The identity of the products was confirmed by GC mass spectroscopy.

The conversion of cyclohexane was 28% and the yield of the mixture of cyclohexanone and cyclohexanol was 24% wt.

We claim:

1. An improved process for the oxidation of cyclohexane to a mixture of cyclohexanone and cyclohexanol which comprises (a) reacting cyclohexane with molecular oxygen in the presence of a solid catalyst containing a phthalocyanine or porphyrin complex of a transition metal wherein some or all of the hydrogen atoms of the said transition metal complex have been substituted by one or more electron withdrawing groups, said transition metal rendering the catalyst insoluble in said cyclohexane and said mixture, said electron withdrawing groups being selected, and sufficient of said groups having been substituted for the hydrogen atoms, to provide the catalyst with enhanced activity and stability in catalyzing the cyclohexane to said mixture as compared to a catalyst comprising the transition metal complex wherein the hydrogen atoms have not been substituted, said process being conducted at a temperature in the range of 20° C. to 80° C., and at a pressure in the range of 5 to 1000 psi; and (b) isolating the cyclohexanone and cyclohexanol formed in step (a).

2. An improved process according to claim 1, wherein the transition metal is selected from the group consisting of iron, cobalt, copper, chromium, manganese and mixtures thereof.

3. An improved process according to claim 1, wherein the electron withdrawing groups comprise a halogen, a nitro group, a cyano group or mixtures thereof.

4. An improved process according to claim 1, wherein the source of molecular oxygen is oxygen, air or a mixture of oxygen and an inert gas.

5. An improved process according to claim 1, wherein the oxidation reaction is carried out in the presence of a solvent selected from the group consisting of acetonitrile, methanol, butanol and cyclohexanol.

6. An improved process according to claim 1, wherein the oxidation reaction is carried out in the pressure of a promoter selected from the group consisting of alkyl hydroperoxide, dialkyl peroxide and mixtures thereof.

7. An improved process according to claim 6, wherein the concentration of the promoter in the reaction mixture does not exceed 1% by weight of the cyclohexane.

8. An improved process according to claim 1, wherein the organotransition metal complex is encapsulated in a solid matrix.

9. An improved process according to claim 8, wherein the solid matrix is an inorganic oxide selected from the group consisting of silica, alumina, aluminosilicates and molecular sieves.

10. An improved process according to claim 9, wherein the solid matrix is an organic polymer.

11. An improved process according to claim 9, wherein the solid matrix contains both an inorganic oxide and an organic polymer.

* * * * *